US008637270B2

(12) United States Patent
Kidwell

(10) Patent No.: US 8,637,270 B2
(45) Date of Patent: Jan. 28, 2014

(54) FLUIDIZED BED DETECTOR FOR CONTINUOUS, ULTRA-SENSITIVE DETECTION OF BIOLOGICAL AND CHEMICAL MATERIALS

(75) Inventor: David A Kidwell, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 873 days.

(21) Appl. No.: 12/618,180

(22) Filed: Nov. 13, 2009

(65) Prior Publication Data

US 2010/0124762 A1 May 20, 2010

Related U.S. Application Data

(60) Provisional application No. 61/114,623, filed on Nov. 14, 2008.

(51) Int. Cl.
*C12Q 1/04* (2006.01)
*G01N 21/53* (2006.01)
*G01N 33/533* (2006.01)

(52) U.S. Cl.
USPC ............ 435/29; 422/82.05; 436/501

(58) Field of Classification Search
USPC ............ 422/82.05; 435/29; 436/501
See application file for complete search history.

(56) References Cited

U.S. PATENT DOCUMENTS

| | | | |
|---|---|---|---|
| 4,939,087 A | 7/1990 | Van Wie et al. | |
| 6,136,197 A | 10/2000 | Egorov et al. | |
| 6,153,113 A | 11/2000 | Goodrich et al. | |
| 6,159,378 A | 12/2000 | Holman et al. | |
| 6,506,584 B1 | 1/2003 | Chandler et al. | |
| 2004/0009529 A1 | 1/2004 | Weimer et al. | |

OTHER PUBLICATIONS

Fujimoto et al. 1994. Fluorescence and Photobleaching Studies of Methylene Blue Binding to DNA. J. Phys. Chem., vol. 98, pp. 6633-6643.*
Kidwell et al., "Concentration of Trace Water Contaminants from Large Volumes of Water with a Fluidized Bed," Poster presented at the 2007 Scientific Conference on Chemical and Biological Defense Research, Timonium MD, Nov. 13-15, 2007.
Kidwell et al., "Continuous Concentration of Trace Materials from Large Volumes of Water with a Fluidized Bed," Presented at the DTRA/JSTO/CBDP Chemical and Biological Defense Physical Science and Technology (CBDP S&T) Conference, New Orleans, Louisiana, Nov. 17-21, 2008.

* cited by examiner

*Primary Examiner* — Jon P Weber
*Assistant Examiner* — Kailash C Srivastava
(74) *Attorney, Agent, or Firm* — US Naval Research Laboratory; Rebecca L. Forman

(57) ABSTRACT

The present invention is generally directed to a fluidized bed detector for continuous detection of biological and chemical materials comprising a fluidized bed of detecting elements suspended in a continuous flow system wherein the detecting elements remain in the system when a first force trying to move the detecting elements to the bottom of the system is balanced with a second opposing force of a flowing gas or liquid trying to move detecting elements to the top of the system and wherein the presence of a target molecule in the flowing gas or liquid disrupts the balance of the first and second forces causing the detecting element to exit the system. The release of the detecting element indicates the presence of the target molecule and may be captured, concentrated, or both for further evaluation by other assays or other means. Also disclosed is the related method of detecting biological and chemical materials using a fluidized bed detector.

10 Claims, 13 Drawing Sheets

(a) (b)

FLUIDIZED BED DETECTOR FOR CONTINUOUS, ULTRA-SENSITIVE DETECTION OF BIOLOGICAL AND CHEMICAL MATERIALS

PRIORITY CLAIM

This Application claims priority from U.S. Provisional Application No. 61/114,623 filed on Nov. 14, 2008 by David A. Kidwell, entitled "FLUIDIZED BED DETECTOR FOR CONTINUOUS, ULTRA-SENSITIVE DETECTION OF BIOLOGICAL AND CHEMICAL MATERIALS," the entire contents of which are incorporated herein by reference.

BACKGROUND OF THE INVENTION

1. Field of the Invention

The present invention relates generally to detectors based on binding events and, more specifically, to fluidized bed detectors for continuous, ultra-sensitive detection of biological and chemical materials.

2. Description of the Prior Art

There is a continued need for sensors for materials such as chemicals, bacterial toxins, and viruses at small concentrations in a large volume of media, where media may be defined as a solvent, such as water, a solid, or a gas or a mixture of media such as food which contains all three states. Some substances that affect biological function are known, so that specific detectors are possible, and some are unknown, so only living organisms can be the sentinel detector. Much effort has been and is being spent on assays for these materials that employ living cells, such as bacteria, mammalian cells, or small organisms as the detection element. The classic example is the use of canaries in mines to detect harmful gases. Because the canaries have a smaller body mass than humans and a higher respiratory rate, they tend to succumb first if harmful gases are present. Live bioassays have a number of issues that limit their use. (1) The living organism must be kept alive. This requires some care and feeding even when the "sensor" is not being actively used. (2) Live bioassays that use complex organisms (such as canaries) may respond to other factors that do not cause appreciable concern for humans, such as temperature and transportation stress. (3) Interpretation of the response of the complex organism may be difficult in varying environments. For example, why did the canary die? Was it a toxic substance in the air, heat stress, or an avian virus that only affects canaries but not humans or other species? (4) For cell-based live assays, the cells also must be kept alive and more importantly some transduction mechanism must be engineered into the cells to identify the threat. For example, the transduction mechanism may be the production of green fluorescent protein or firefly luciferase in response to certain substances. In these cases, the cells would be monitored for an increase in fluorescence or light emission upon addition of suitable substrates. Although such a cell-based, live bioassay can be useful, each organism must be engineered to respond to a unique substance, which can be a daunting task if the agent in question does not have a known signaling pathway.

If the agent in question is known, specific detectors are possible. They may be either based on immunoassays, where the antibodies or other specific binding molecules such as peptides can act as the recognition element, or nucleic acid detectors where specific sequences of DNA or RNA are sought. The major issue with many specific detectors is that the volume of liquid or air testable is quite small so that a preconcentration step is required. Without this preconcentration step, the likelihood of detection of a target species decreases with the concentration and the volume of material needed for the test (see FIG. 1). Because of this preconcentration step, the testing technology is often a grab-and-sample type of test, i.e., the preconcentrator is run for a given amount of time, a sample of the concentrate is taken, and the sample tested. This process can be repeated on a periodic time scale but as most tests are single-use tests where consumption of reagents can be substantial so that the frequency of testing is often limited. Most immunoassays are single use; an example being the lateral-flow immunoassays used in home-pregnancy testing. An exception is displacement assays such as the flow-immunoassay described in Kusterbeck et al., "A continuous-flow immunoassay for rapid and sensitive detection of small molecules," *Journal Of Immunological Methods*, 135, 191-197 (1990), the entire contents of which are incorporated herein by reference. Displacement assays, although proposed here as well, are not as sensitive as completion or sandwich immunoassays due to kinetics and antibody affinity. For high sensitivity, the antibody binding constant must be as high as possible. However, tight binding means slow release so that the displacement with a test antigen either is slow or requires high levels of antigen.

U.S. Patent Application 20040009529 by Weimer et al. (Jan. 15, 2004), the entire contents of which are hereby incorporated by reference, describes a process for the capture of antigens on beads in a flow-though module. This is not a continuous assay as the captured antigens must be detected, (for example with an enzyme—linked antibody) in a grab and sample mode. The particles are not released upon binding to the antigen. This system is similar to the BEADS (Biodetection Enabling Analyte Delivery System) sample preparation technology described in the next paragraph.

U.S. Pat. No. 6,506,584 to Chandler et al. (Jan. 14, 2003), U.S. Pat. No. 6,159,378 to Holman et al. (Dec. 12, 2000), and U.S. Pat. No. 6,136,197 to Egorov et al. (Oct. 24, 2000), the entire contents of each are hereby incorporated by reference, describe PNNL's BEADS (Biodetection Enabling Analyte Delivery System) sample preparation technology. Although claimed as a fluidized bed for rapid kinetics, PNNL does not use a force field to retain the particles but rather a complex capture and release system for the particles to maintain them in a fluidized state. Like the Weimer application, the BEADS system is more a grab and sample system. Furthermore, in the way that the particles are retained (like a simple screen), the BEADS system cannot handle complex media, such as food, as it will quickly plug.

U.S. Pat. No. 6,153,113 to Goodrich et al. (Nov. 28, 2000), the entire contents of which are hereby incorporated by reference, uses a continuous centrifuge and binding particles. However, it is not a detector and it does not release the particles upon binding. Rather the particles only act as a capture medium to remove a selective blood component from the incoming fluid with purification of the fluid (blood in this case) as the goal.

U.S. Pat. No. 4,939,087 to Van Wie et al. (Jul. 3, 1990), the entire contents of which are hereby incorporated by reference, describes the use of a centrifugal reactor for culturing cells and harvesting high-valued proteins in a continuous manner. This patent shows that a centrifugal reactor can maintain living cells on a long-term basis. However, it is not used as a detector.

BRIEF SUMMARY OF THE INVENTION

The aforementioned problems are overcome in the present invention which provides a fluidized bed detector for continuous detection of biological and chemical materials comprising a fluidized bed of detecting elements suspended in a continuous flow system wherein the detecting elements remain in the system when a first force trying to move the detecting elements to the bottom of the system is balanced with a second opposing force of a flowing gas or liquid trying to move detecting elements to the top of the system and wherein the presence of a target molecule in the flowing gas or liquid disrupts the balance of the first and second forces causing the detecting element to exit the system. The release of the detecting element indicates the presence of the target molecule and may be captured, concentrated, or both for further evaluation by other assays or other means. Also disclosed is the related method of detecting biological and chemical materials using a fluidized bed detector.

The present invention generally relates to a continuous flow sensor based on a fluidized bed. This sensor can operate with living cells or inert particles as the detecting elements for target materials. In many modes of operation, no routine maintenance would be necessary as supplies are not depleted unless a detection event occurs. The sensor can operate with high flow rates, which mitigate the need for separate large, power-hungry pre-concentration schemes. Such a sensor should find wide deployment in the monitoring of the nation's air, water, food, and agricultural areas for the presence of biological and chemical threats.

Some of the advantages of the Fluidized Bed Detector are:
- It can detect low target numbers—a single binding event/mL is possible because single-particle labels are readily detectable.
- It can be multiplexed by having different labels on each particle corresponding to different antibodies/DNA.
- It can handle high flow rates (liters/hour), which reduces the need for pre-concentrators (some fluid can be re-circulated, if necessary).
- It is a continuous flow system—no wait for the detection event—detection in minutes.
- It requires no addition of reagents—once started the particles are retained—some fluid make-up (i.e. saline) may be necessary in certain modes of operation.
- The rapid particle collisions allow shear (the magnitude of which can be controlled) thereby providing selectivity over non-specific agglutination.
- It can be operated in the presence of a high particle count media as the flow channels are not restricted nor are filters necessary to remove debris, which avoid plugging or replacement of the filters.

The fluidized bed detector (FBD) of the present invention is quite distinct from xMAP® technology pioneered by Luminex using a Coulter counter in that xMAP is not continuous and cannot handle very large numbers of particles nor a large volume of solution and must count many particles rather than the small number in the FBD. Additionally, the xMAP technology does not concentrate species, once detected. In one version of the xMAP system, the particles are fluorescently labeled and coated with fluorescent dyes such that the classes of particles are distinguishable. For example, two fluorescent dyes may be employed that have distinct emission characteristics. The ratio between the two dyes allows different classes of particles to be distinguished. The classes of particles have antibodies on the surface. The test antigen may be fluorescently labeled. After mixing with the test antigen, the whole mixture is passed though a Coulter counter, where each particle is examined. The two labels tell the class of particle and the remaining fluorophor would be present if the antigen were present. Note in this scheme, a large number of particles need to be counted as only a few would have the antigen. Additionally, the antigen must be labeled with another fluorophore, which could be a second antibody, and the reagents are used for each assay and cannot be easily recycled. Furthermore, the principle of the Coulter counter is to pass the particles through a relatively small hole to separate them one at a time so that each may be interrogated. Such a hole is easily plugged by particles in the test matrix and the therefore, solids or slurries cannot be handled.

The FBD could use a similar particle-labeling scheme to Luminex for multiplexing, but that is where the similarity ends. No small holes are necessary to sort the particles as the release per unit time should be limited. Also, the FBD may use two distinct fluorophore containing particles that cross-link. In that case, only particles would be counted that have both fluorophores present in the complex. This scheme will provide better specificity as it avoids counting particles that leak from the system as leaking particles would have only one distinct fluorophore pattern present.

These and other features and advantages of the invention, as well as the invention itself, will become better understood by reference to the following detailed description, appended claims, and accompanying drawings.

BRIEF DESCRIPTION OF THE DRAWINGS

FIG. 2(a) shows a particle capturing a bacteria wherein the complex is lost from the top as density decreases and FIG. 2(b) shows DNA linking two particles wherein the complex is lost from the bottom as density increases.

FIG. 5(a) shows the brown dirt without dyed polystyrene particles. FIG. 5(b) shows polystyrene particles with the "dirt" flowing through as a brown haze in the top of the flow-cell. FIG. 5(c) shows the same polystyrene particles when the dirt was removed. The pictures were taken with a strobe light as the centrifuge was continually moving, and the flow was also continuous to fluidize the particles.

FIG. 6(*a*) shows a two-dimensional flow cell, partially filled with a liquid to highlight the cylindrical shape. FIGS. 6(*b*)-(*j*) have square sides.

DETAILED DESCRIPTION OF THE INVENTION

The Fluidized Bed Detector (FBD) of the present invention is basically a system containing detecting elements wherein the detecting elements are suspended in the system using electrical fields, magnetic fields, acceleration forces, or any combination thereof to retain the particles against a counter-flow of a fluid such as a liquid or gas containing the target of interest. In one embodiment, the system could be a centrifuge (to increase sedimentation rates) using centrifugal force to counterbalance the force of the fluid flow. Detection particles are initially introduced into the analysis chamber by flowing them into the bottom while the chamber is spinning. The forces acting in the FBD can be mathematically modeled with equations 1-3. The particles are retained in the spinning chamber by the balancing of two forces: the centrifugal force (equation 1) (this could also or alternatively be a magnetic or electrical field or a gravitational force), which causes the particles to exit the outside (bottom) of the spinning chamber, and the fluid flow (equation 2), which causes the particles to exit the inside (top) of the chamber. When these two forces are in balance (equation 3), no particles exit the chamber—only the flowing liquid (which may contain the targets of interest) exits the top and bottom. When there is a target molecule in the fluid flow, the balance of the two forces is disrupted causing the detecting element to exit the chamber. The balance of the forces can be disrupted by a cell being killed (the cell is the detecting element), by the binding of the target to the detecting element, the cross linking of two particles, or two particles previously cross-linked breaking apart.

Figure 1:
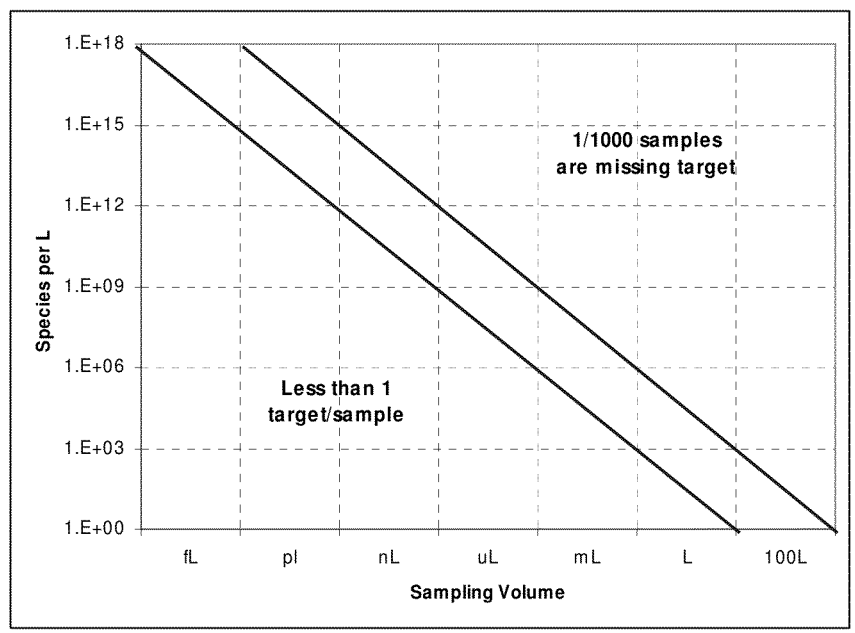
FIG. 1 shows the probability of detection a bacterial spore verses sample volume. The lines enclose a probability of from 1% to near 100% detection window. For example, if the sampling volume was 1 µL, to reach 1 species in that volume one would need to have over 1e6 species/L (see K. E. Petersen et al., "Toward Next Generation Clinical Diagnostic Instruments: Scaling and New Processing Paradigms," *Biomedical Microdevices*, 1, 71-79, (1991) the entire contents of which are incorporated herein by reference).
Figure 2:
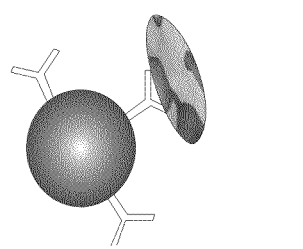
FIG. 2 shows two examples of particles interacting with biomolecules.
Figure 2:
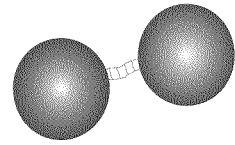

These two forces have different physical sources. Movement by the centrifugal force depends on the density of the particles relative to the fluid. Movement by the fluid flow depends on the average face area (surface area projected along the fluid flow) of the particles. During the detection event, the particles change their density relative to their face area. (Face area is the area projected into the flow. For a sphere this area is just a circle with the same diameter as the sphere. For a cylinder, it is a complex function of the tumbling rate and end area.) Two examples of how interacting particles can change their density relative to face area are shown in FIG. 2. The cause of this change depends on the type of assay and particles being employed. Once this change occurs, the centrifugal and flow forces are no longer balanced and the particle leaves the centrifugal chamber (either though the bottom or top) where it is detected by some means, for example absorption, fluorescence, change in magnetic signature (such as a magnetic particle changing the impedance of a coil), colorimetric assay, etc. Because single particles can be readily counted and measured, a change in a single particle, of the many suspended in the chamber, may be detectable. Unlike many assays that rely on binding of antibodies or nucleic acids to surfaces and binding of the target to those species, the fluidized bed is well mixed by the incoming flowing stream so that kinetics are rapid. Additionally, a large excess of particles may be present allowing more rapid kinetics due to concentration effects without compromising sensitivity. (For example, in competitive immunoassays, the greatest sensitivity is found when the concentration of the antibody is one-half the concentration of the analyte (due to antibodies having two binding sites). As immunoassay kinetics requires two entities to interact, the reaction rate is dependent on both the concentration of the analyte and antibody (a second order reaction). Therefore, the time for interaction must increase as the inverse square of the analyte concentration.)

(1) Force on particle due to centrifugal force:

$$F_{centrifugal} = mr\omega^2 = \frac{\pi d_{particle}^2}{6}(\rho_{particle} - \rho_{medium})(r\omega^2)$$

(2) Force on particle due to fluid flow:

$$F_{StokesDrag} = 3\pi\mu d_{particle} v_{particle}$$

(3) Balanced when equal:

$$v_{particle} = \frac{d_{particle}^2}{18}(\rho_{particle} - \rho_{medium})r\omega^2$$

Figure 3:
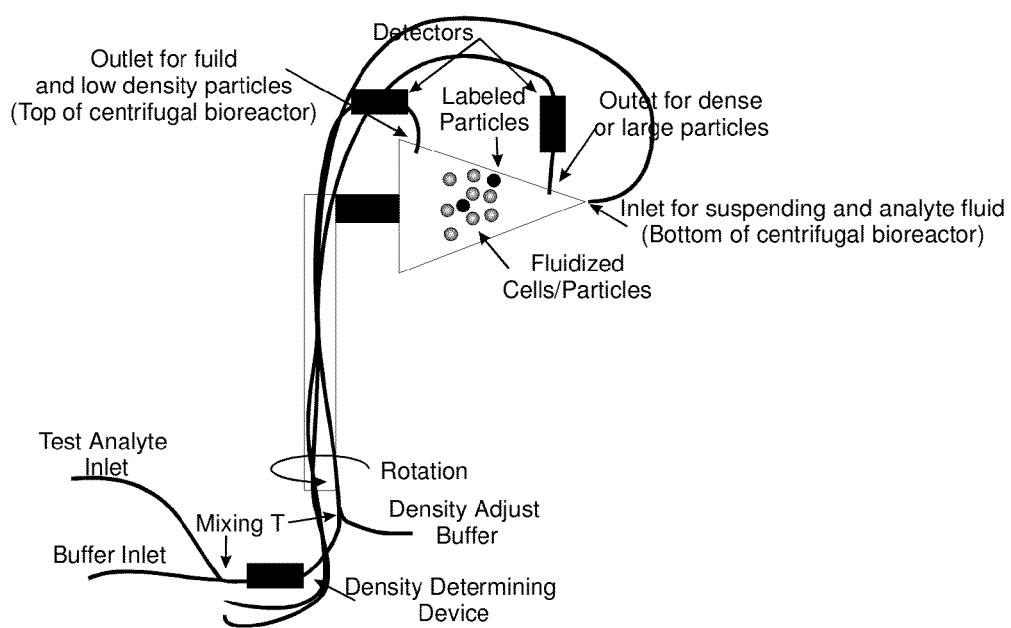
FIG. 3 is a schematic diagram of the fluidized bed detector, which has no rotating seals. The hoses are protected from twisting by a counter rotation at the base. (See, e.g., U.S. Pat. No. 6,153,113 to Goodrich et al. (Nov. 28, 2000), U.S. Pat. No. 4,425,112 to Ito (Jan. 10, 1984), and U.S. Pat. No. 4,114,802 to Brown (Sep. 19, 1978), the entire contents of each are incorporated herein by reference.)
Figure 4:
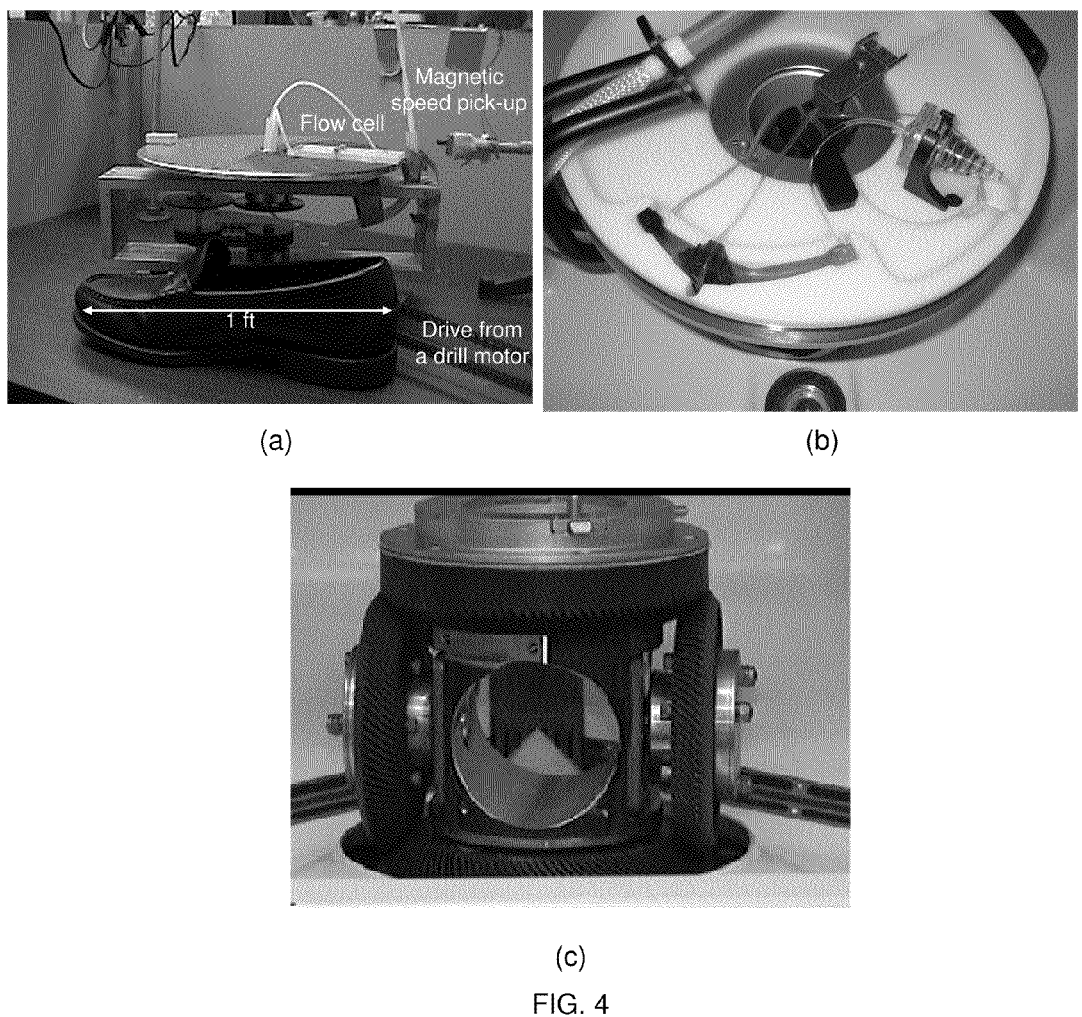
FIG. 4 shows (a) one embodiment of the fluidized bed detector; (b) an embodiment that could be a commercial system, which is the inside of the Amicus Separator (one example is the Amicus Separator at: http://www.baxterfenwal.com/jsp/products/productDetail.jsp?prodid=159&familyid=36); and (c) a side view of the commercial system showing the precision gearing used for faster speeds and balance.

$d_{particle}$ = diameter $\rho$ = density $\omega$ = radians/sec $v$ = velocity $\mu$ = viscosity $r$ = centrifuge radius FIG. 3 shows the basic concept for the FBD using labeled particles. The particles may be either living cells or inert particles. FIG. 4 shows the model FBD constructed for preliminary testing and the inside of a commercial unit used for blood processing. The commercial unit employs balances and precision gears to rotate the upper stage at twice the rotational speed as the arm.

A preliminary system used belts and a variable-speed drill motor to turn the main centrifuge. The speed was controlled with a laboratory Variac and not automatically stabilized (the user needed to make small adjustments until the desired speed was obtained). The speed was monitored using a magnetic pick-up Reed switch with a permanent bar magnet mounted on the rotor arm. The signal from the switch triggered a strobe light, which allowed movies to be made of the flow, and was also fed into a RS232 port of a computer. The signal into the RS232 port provided the start bit for pseudo-character (basically read as the ASCII Null character), which was read by the computer. The timing between characters was measured and averaged every few seconds (the program allowed variable averaging) to report the RPMs of the centrifuge. With this preliminary system, 1000 RPM movement could be generated. With the center of the cell at an average distance of 19 cm, this would produce 112 g force on the particles at 1000 RPM. Better balancing of this preliminary design may allow faster speeds and is important as the g force increases as the square of the rotational velocity. The higher the g force, the better the resolution between two objects. Commercial systems can achieve over 6000 RPM.

Figure 5:
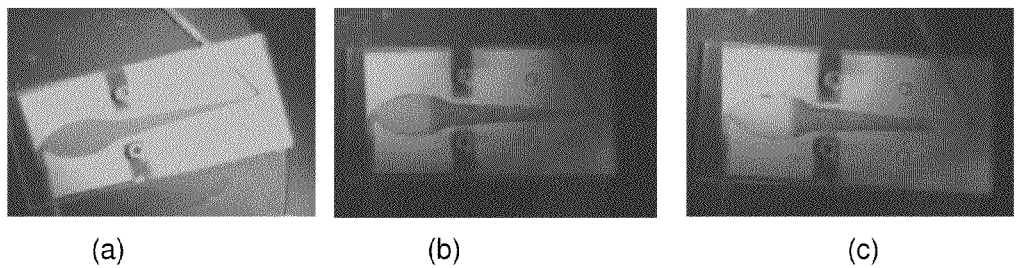
FIG. 5 shows a test done with iron-oxide particles. Iron-oxide particles as model "dirt" flowed through the cell while red-dyed polystyrene beads were retained. Although more dense, the "dirt" being too small (1-2 µm) was not retained under the conditions used.
Figure 6A:
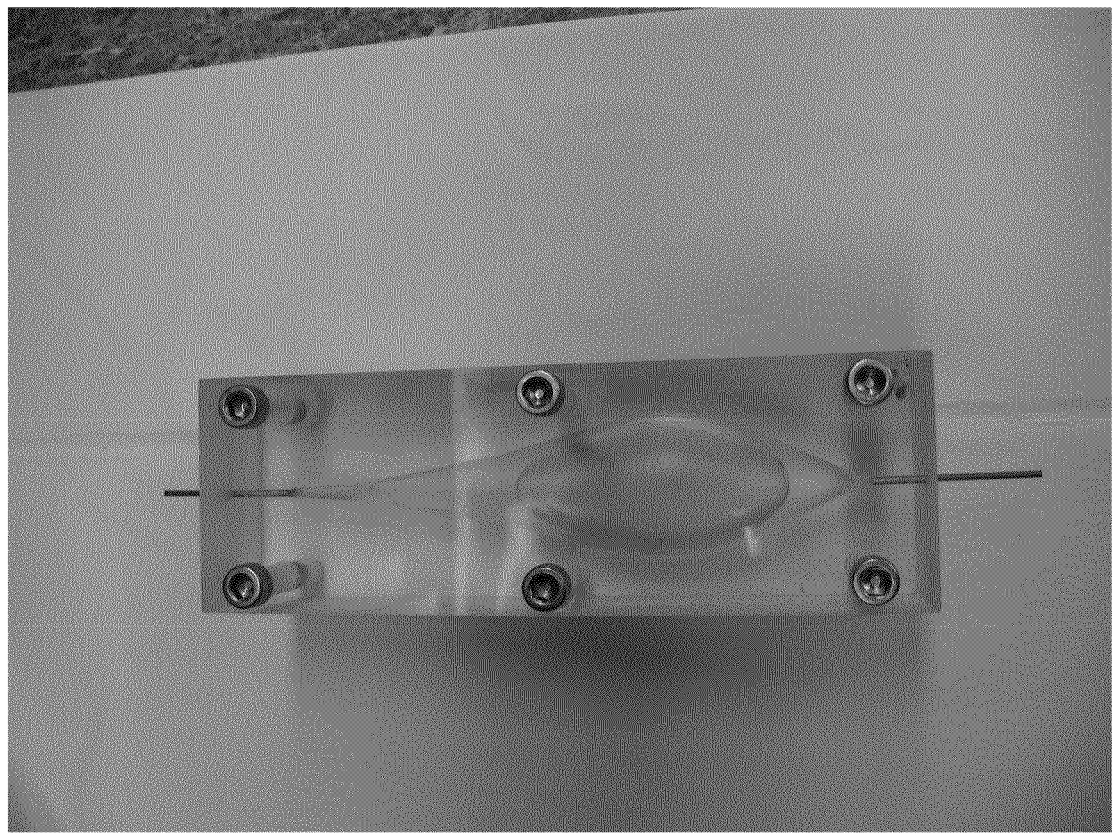
FIG. 6 shows some representative flow cell designs. Flow cells were filled with a colored dye to highlight the shape.
Figure 6B:
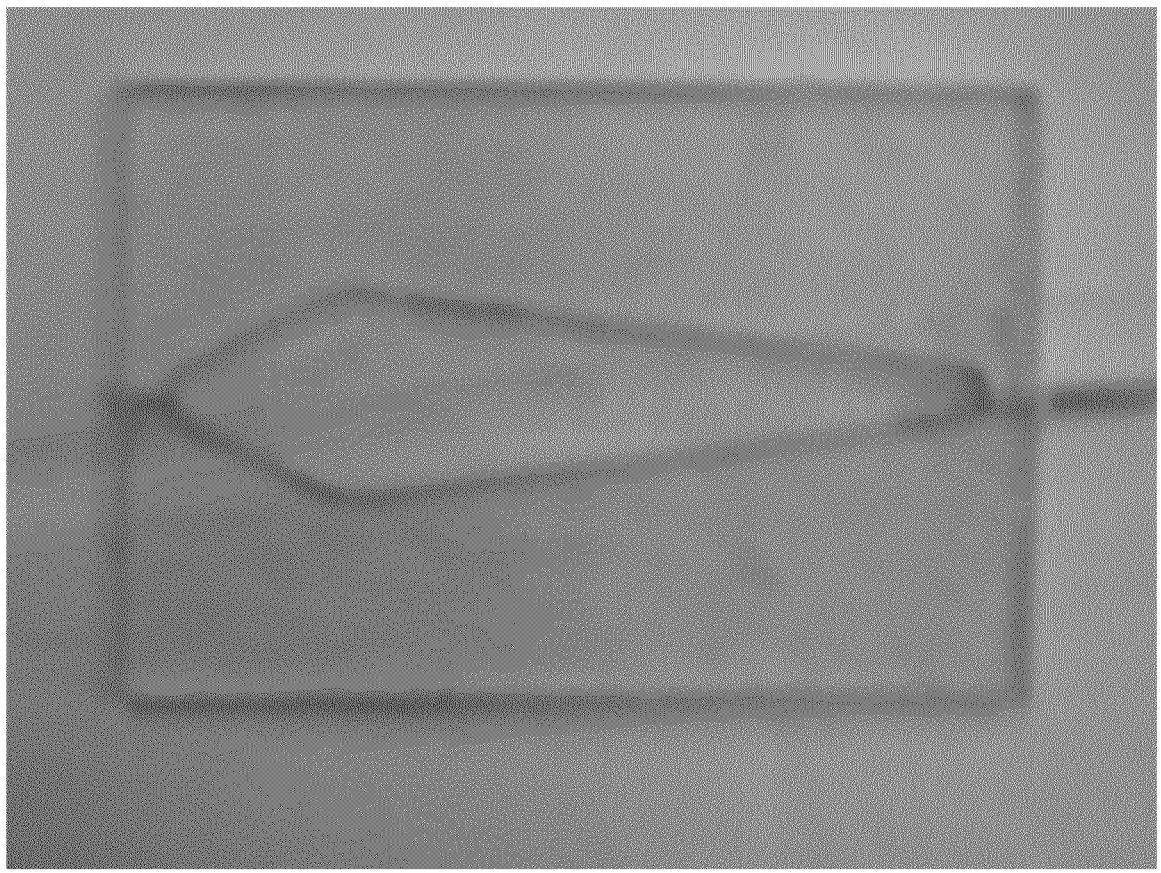
Figure 6C:
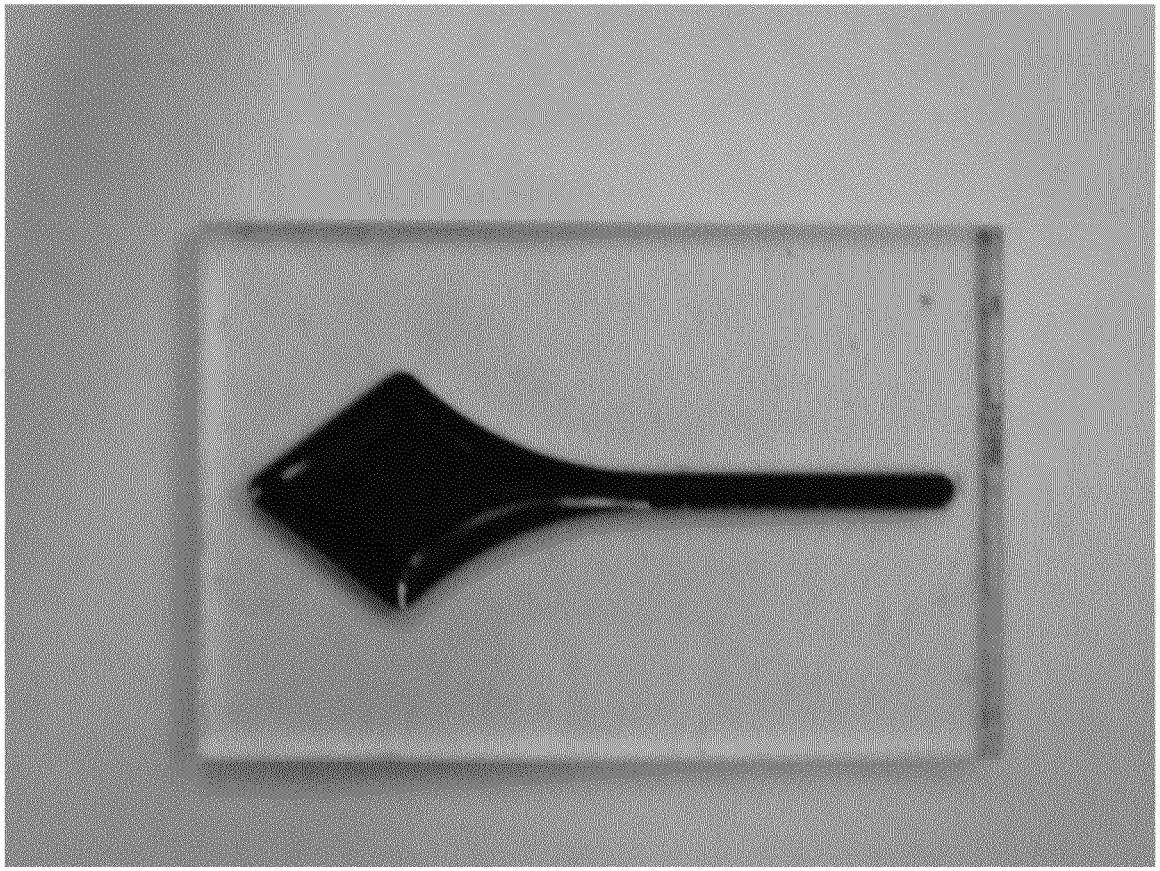
Figure 6D:
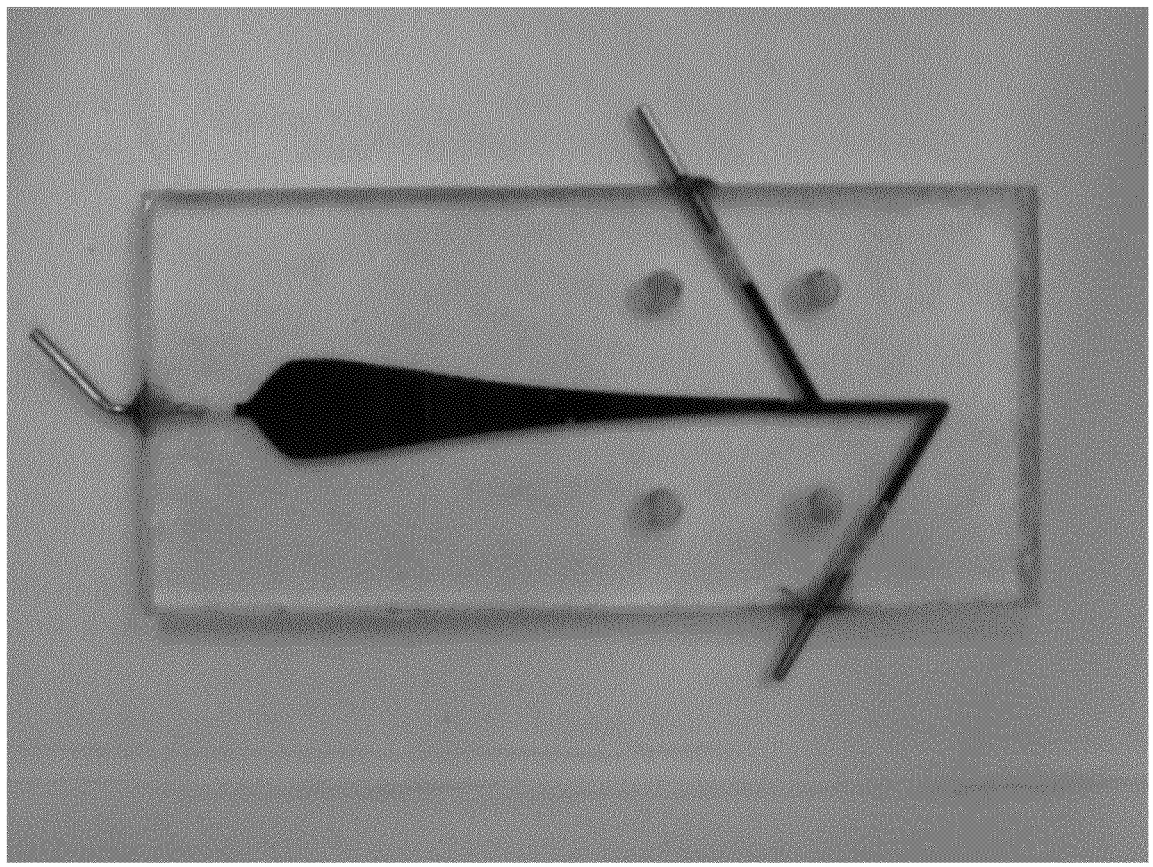
Figure 6E:
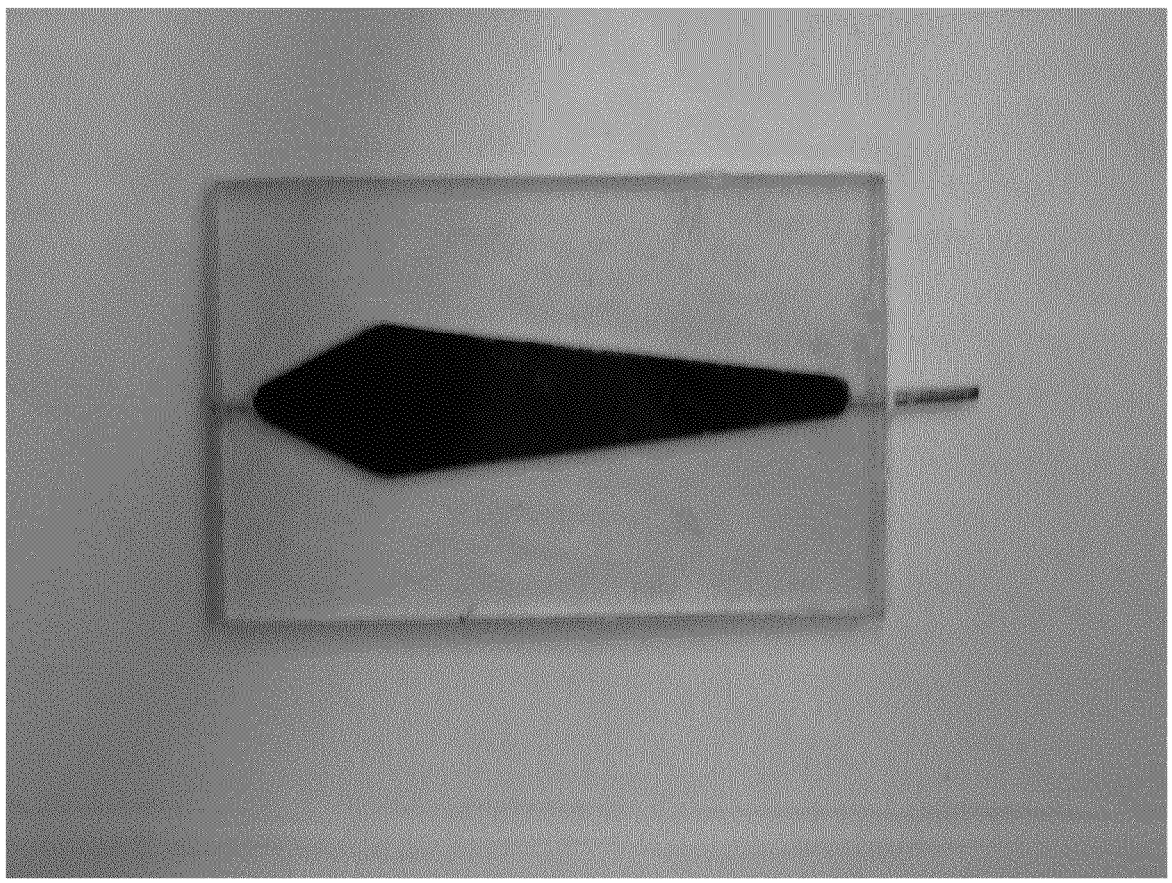
Figure 6F:
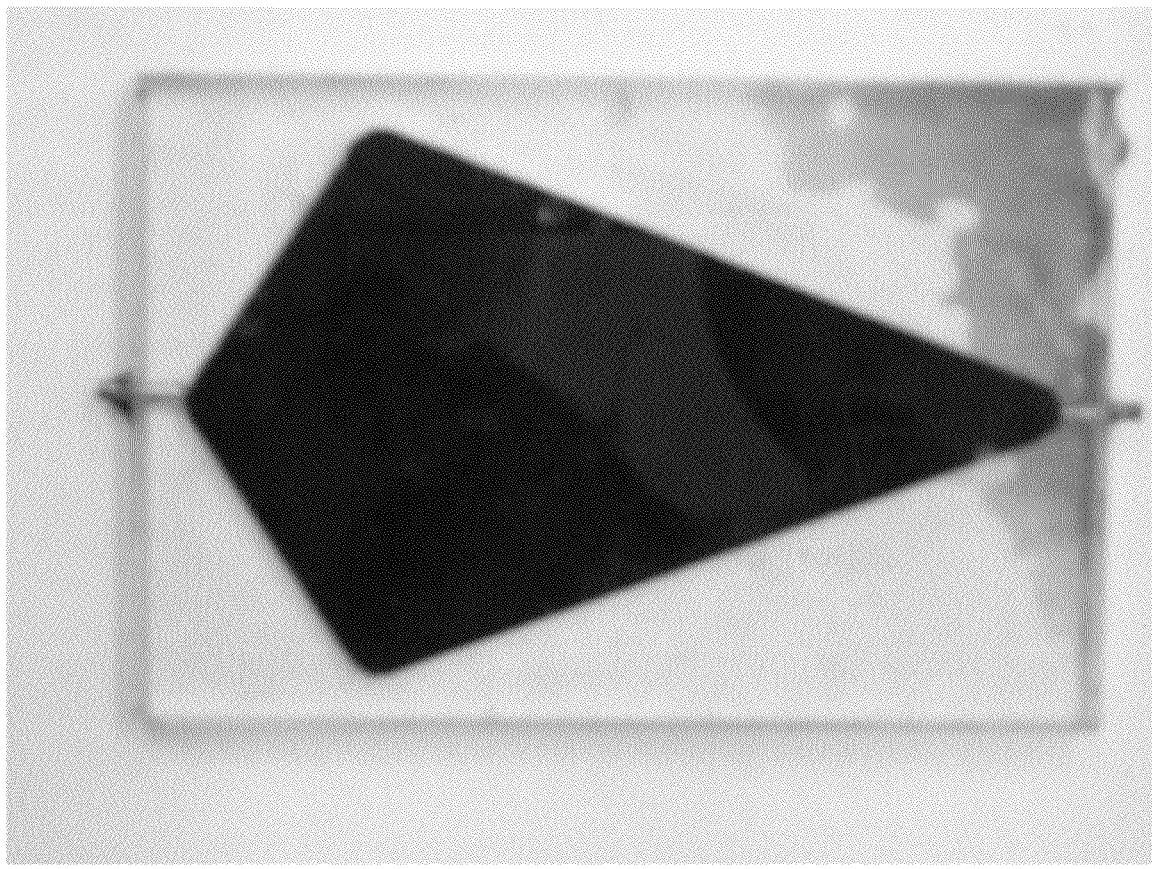
Figure 6G:
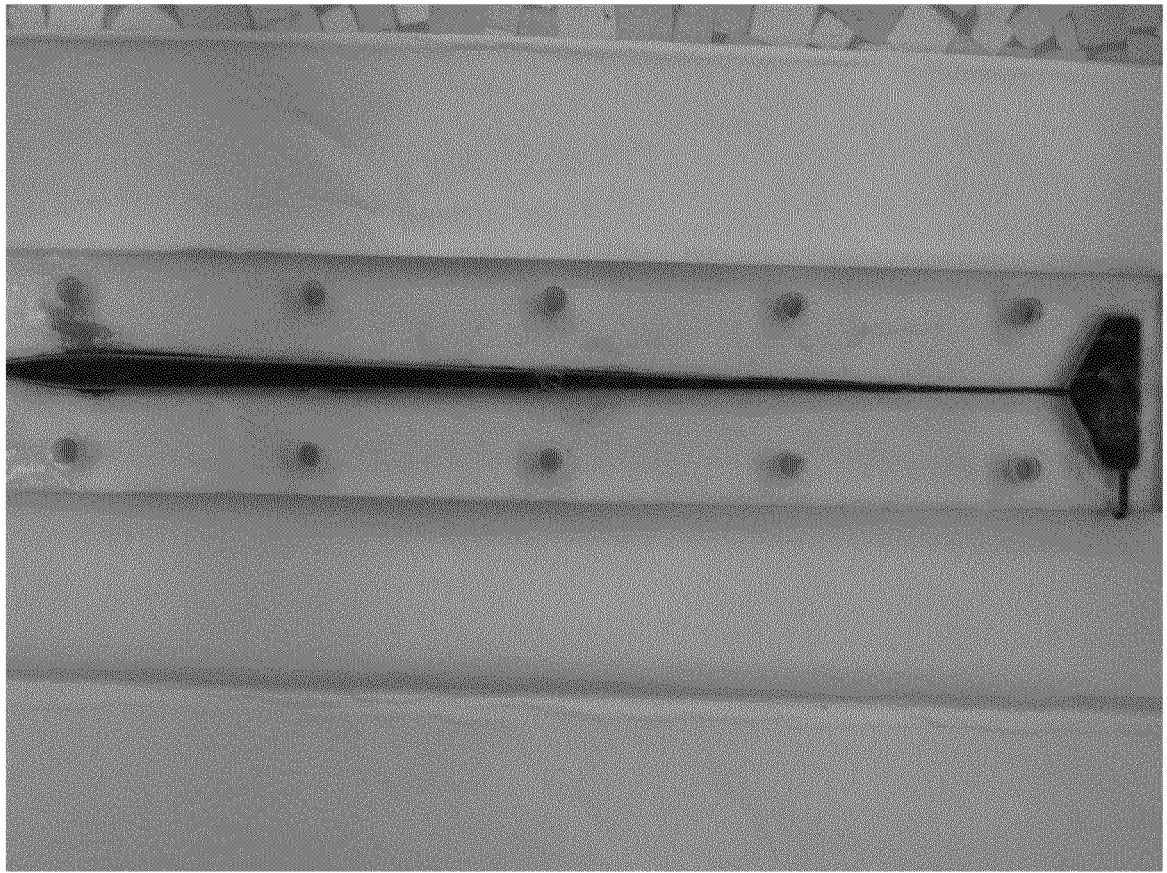
Figure 6H:
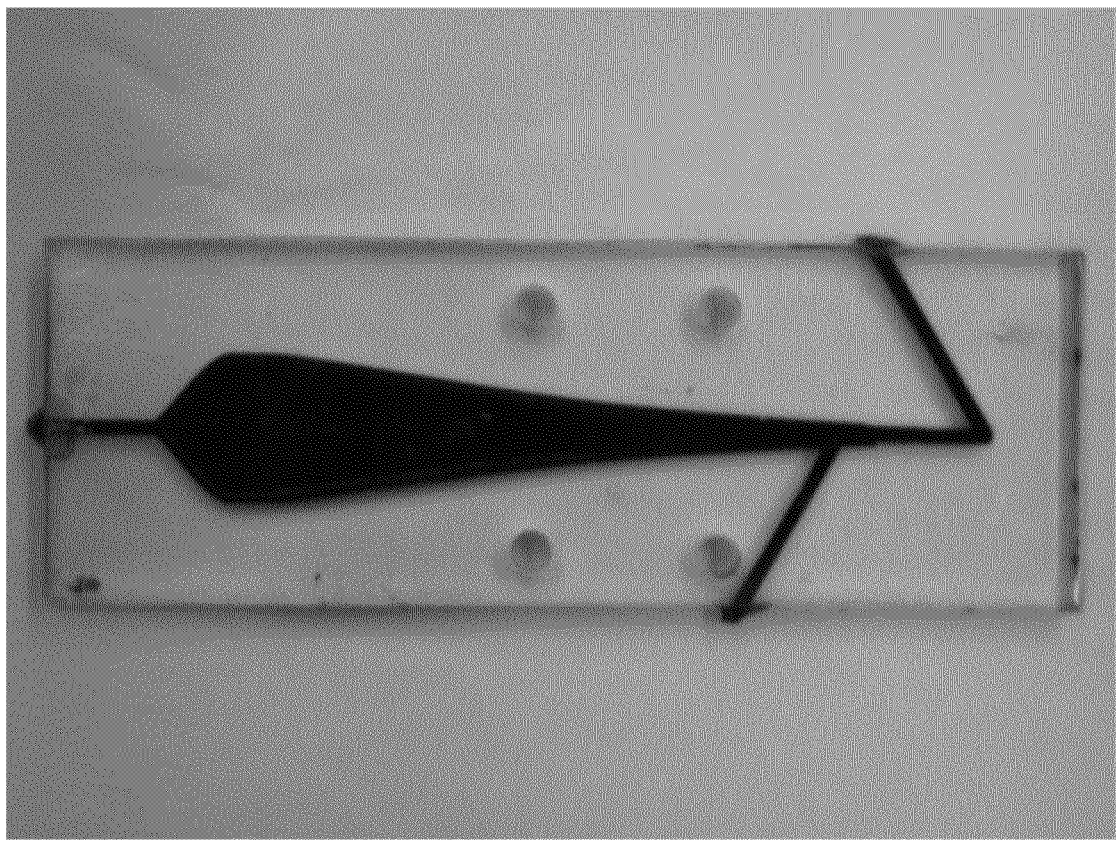
Figure 6I:
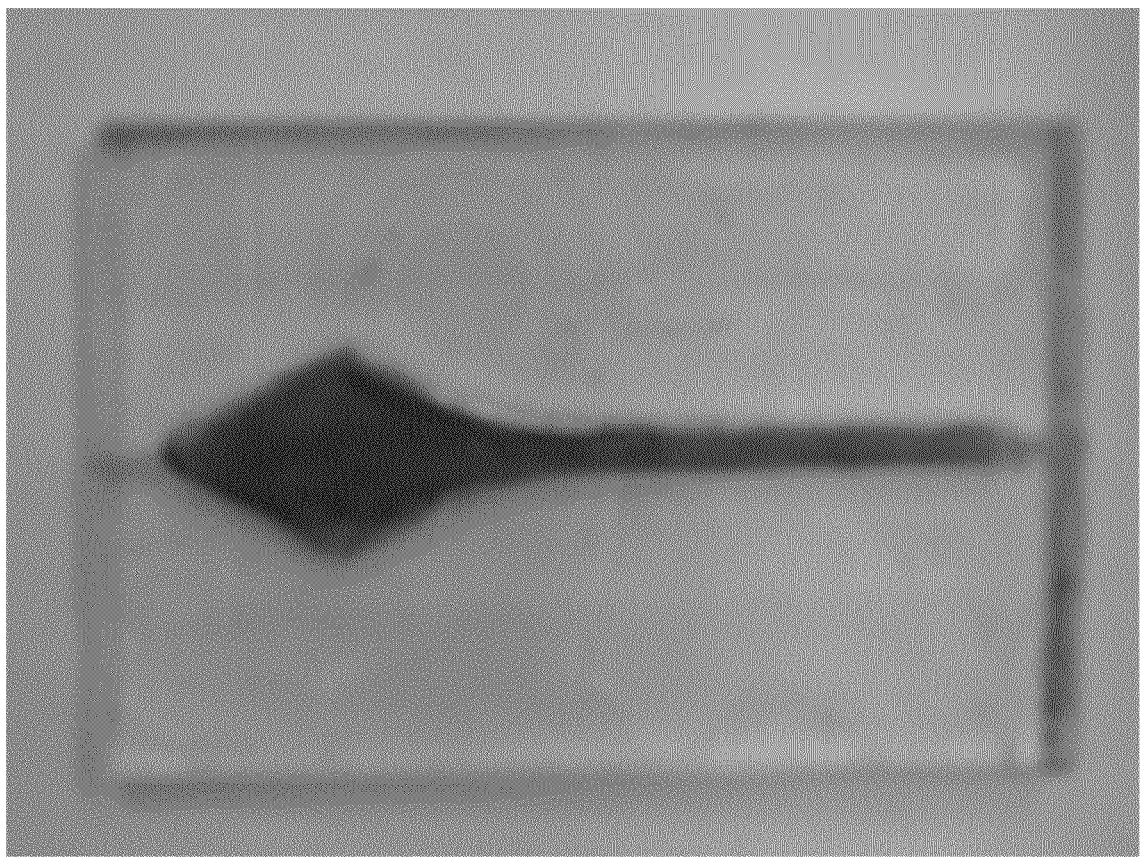
Figure 6J:
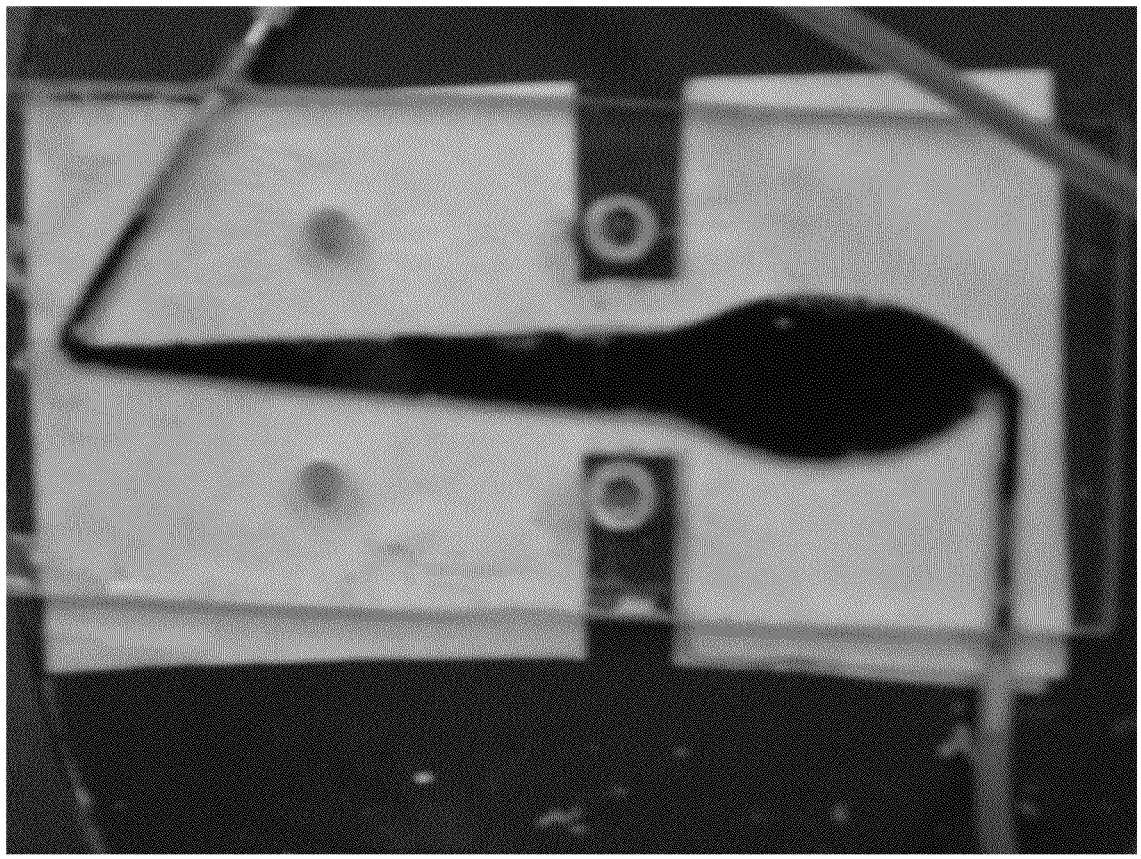

One advantage of the FBD system of the present invention over other fluidized bed collection schemes is that debris does not have to be separated before the sample is tested. Many test samples, such as food, contain particles or debris that are not of interest. For most flow-though assays, these particles must be separated either with filters or by centrifugation before the sample is assayed or the particles will interfere. The FBD does not have this requirement. There are no filters, small paths, or sharp angles to plug in the FBD. The path is continuous. Only those particles meeting the density-size-flow balancing will be retained. By using particles as the detection element in the FBD they have the advantage over living cells in that they can be engineered to have a wide range of densities that can then handle a wide range of fluid flows and discriminate against nuisance particles. For example, FIG. 5 shows the flow of colloidal ion particles (used as models of dirt and for their color) through the FBD while retaining the latex beads. Milk (high protein content and homogenized particles), diluted tomato paste, and diluted ketchup were run though the FBD while retaining the latex beads being tested as sensors. The tomato paste and ketchup left some strands of pulp indicating that a higher flow with denser sensor particles would have been advantageous. The FBD may be very useful in food testing for bacteria as a large number of samples can be tested quickly in a flow system and allowing isolation of particles that may be cultured for confirmation of the presence of a certain bacterial species.

Another advantage of the FBD, is that upon release of the detecting element, the released detecting element selectively can be captured, separated, concentrated, analyzed, or any combination thereof. When the detecting element is released, it carries with it the target material. When detected, the detecting element can be shunted selectively into a collection system for further analysis or disposal where the other components of the test matrix are shunted for disposal or further analysis. This selective separation ability provides the opportunity to concentrate targets from large volumes as part of the initial warning system.

Particle Based System

The FBD system has flexible requirements for the labels used in the detector. One class of materials could be inert materials such as either polymer or glass based beads. Having the materials homogeneous in diameter and density makes construction easier. The beads have antibodies, nucleic acids, complexes, or any combination thereof on their surfaces, which in the presence of a target molecule either cross-links two or more particles (sandwich assay) or breaks a complex apart (displacement assay). The term antibodies can refer to a number of protein binding molecules such as antibodies, antibody fragments, enzymes, or engineered peptides that selectively recognize other molecules. The term nucleic acids is being used to encompass a wide range of DNA or RNA selective binding molecules—they may also be DNA or RNA bases with non-conventional backbones such as peptide nucleic acids; however, DNA or non-conventional backbones are preferred over RNA as it is more stable in solution. The term complexes can refer to molecules that recognize other small species such as metal ions. Examples may be EDTA, which is selective for calcium or six histidines, which is selective for nickel. For these complexes, the binding of the metal ion is unlikely to change the particle density sufficiently to be useful. Instead, the target metal ion will displace a ligand attached to a larger molecule or particle in a displacement type assay.

Cross linking of two particles changes the average face area to density ratio and the complex will flow out the bottom of the spinning chamber where it is detected by some means, for example fluorescence. Thus, the presence of a large target molecule/species (virus, bacterium, or DNA) that can form a sandwich assay will be detectable by the release of labeled particles. Note that the target is not labeled, so raw material can be analyzed without preparatory steps. The release of labels (fluorescent latex spheres in one configuration) indicates the presence of a given target. Small molecules also can be detected by disrupting (displacement assay) a preformed complex that has the correct buoyancy when two particles are bound together but not when separated. The labeled particles of the disrupted complex would flow out the top (hence a detector on that outlet).

Unlike normal agglutination assays, a single binding event can be detectable. Additionally, unlike surface assays, the fluidized bed is well mixed by the incoming flowing stream so that kinetics of interaction is rapid. Because the measurements are made outside the chamber, a large excess of particles may be present on the inside as these are never seen by the detector, which may be a Coulter counter-like system.

Cell-Based System

Live System

For sentinel systems, it is often useful to have living organisms present as test subjects. Bacteria or human cells are not ideal because they may be killed or react to any number of materials that are not acutely toxic, such as high salt concentrations or pH changes. However, cells are much easier to keep alive than higher order organisms and more can be fit in a given space. Consider the inert particles, discussed above, as replaced by cells. The basic concept is to continuously maintain cells or bacteria in the FBD while outside nutrients and test compounds are introduced. Fluidized beds have been considered for just such a scheme as they allow continual harvesting of valuable proteins that may be secreted by the cells and a constant monitoring of the media (see U.S. Pat. No. 4,939,087 to Van Wie et al., Jul. 3, 1990, the entire contents of which are incorporated herein by reference). The fluidized bed allows greater cell densities to be achieved and faster growth. Although much more complicated than inert particles, living cells could be used in several ways:

Release of Materials

The cells are maintained by their density and size in the system and respond by changing their protein coat or releasing materials when outside compounds trigger some biochemical process. Almost any type of cell response that is selective in the changing environment and occurs on the reporter-cell surface can be detected by this system. For example, when cells die, there density decreases and they would flow out of the FBD. Thus, even responses to viruses would be detectable. The released materials would be detected in the flowing stream by addition of antibodies or by engineering the released materials to be inherently fluorescent or by adding a dye to the exit stream that selectively labels the target cells.

Instead of detecting the released materials in the stream one could combine the living cells with inert particles. If the reporter cells excreted a protein or other large molecule into the medium, this could be detectable by crossing-linking the reporting labels. For example, if the labels were particles of a similar density to the cells and contained antibodies to an excreted protein, say anti-luceferase, then the excreting of the luceferase by the cells would cross-link the reporter particles and cause them to be released (In this case, the reporter particles would likely be latex beads, which are predominately spherical. These complexes are released from the centrifugal reactor because the centrifugal force is no longer counterbalanced by the incoming flowing liquid. The force that the flowing liquid force exerts is based on the face area exposed to the flow where as the centrifugal force acts on the density (which is different, generally higher, than the incoming media otherwise the particles would not move). Cross-linked particles have a higher density to face surface area than do single particles because they do not always face parallel to the incoming liquid (i.e. one particle shields the other). Thus, they will move to the bottom of the FBD.

As envisioned with the FBD, even the presence of DNA or other large molecules that do not affect the cell population could be detectable. In this case, there would be no biological amplification and only a reliance on the cross-linking of the particles would occur.

Release of Dead Cells

Cells that die tend to have a different density then living cells and would be swept from the FBD. The living cells could be stained with a dye upon release and the fluorescence of the stain monitored to essentially count the release vs. time. If a major increase in release is noted, then the death of the cells in the FBD must be from some cause—toxin or virus that would need to be investigated further. One could distinguish the release of cells from the FBD vs. cells present in the feed water by staining or more specifically by antibody interactions. The antibody interactions would allow identification of a number of released cells as the antibodies could be specific to a certain cell type. For example, the cells could be stained with a live-dead stain such as the SYTOX Green Stain sold by Molecular Probes. This stain does not stain cells that have intact membranes. The antibodies may be labeled with a fluorescent dye such as Rhodamine. Only those cells that had both fluorophores present would be considered counted and released. Unfortunately, continual addition of antibodies is expensive unless the antibodies were recovered in the flowing fluid and may not be necessary if the incoming fluid has few cells present that will stain. Stains are relatively cheap. To save resources, one could prestain the incoming fluid but that gets more complex as the stain would be present in the FBD chamber. To be successful, a prestain could be designed to change some property that increases the staining and then reduces it. For example, the incoming test fluid may be adjusted to a low pH, which could increase staining. Then the system is buffered to neutrality when it flows though the FBD chamber. Another stain is added on the outlet that stains everything at neutrality. Only those cells with the second stain and without the prestain would be considered for detection. Alternatively, the incoming fluid may be passed through a bed, such as activated charcoal, to remove the stain but not the potential target toxins. One could also engineer the cells to produce a fluorescent protein and retain it to identify the cell. Each cell type would be engineered to produce a different fluorescent protein.

Release of Cross-linked Cells

Some cellular systems have on their surface receptors and can cross-link in the presence of a given antigen. These receptors may be engineered, as in phage display protein libraries, to be similar to antibodies in their binding, recognition, and specificity. Cross linking of two cells causes their release from the FBD chamber. This system is preferable for ease of detection, but is really no better than the use of inert particles coated with antibodies, as discussed above. In fact, one could use killed cells as the inert particles for cost considerations and just prestain them or have them engineered to be fluorescent.

Flow Cell Design

A number of different flow cells were tested to achieve Laminar flow. Examples are shown in FIG. 6. If the cells had an inlet that went parallel to the axis, i.e. directly into the bottom, the flow was very erratic. Having the inlet with a curved flow helped. Also, having an inlet with a pressure chamber (as shown for the long cell in FIG. 6*g*) helped but the chamber tended to entrap the particles used for labels. The inlet on the cell in FIG. 6*j* was the optimum found for a uniform flow. The centrifugal force decreases as the radius decreases whereas the force due to fluid flow is constant. The flow cell should be tapered to provide stability in retention of the particles as the taper decreases the fluid flow in proportion to the radius. A slightly greater increase in taper than predicted on a quadric exponential was optimum. This shape is shown in FIG. 6*e*. Additional cells with both a taper and a bulb, for particle storage, allow different shear forces depending on the position in the cell.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for detecting biological and chemical materials, comprising:

suspending a fluidized bed of detecting elements in a continuous flow system, maintaining the detecting elements in the system by balancing a first force trying to move the detecting elements to the bottom of the system with an opposing second force of a flowing gas or liquid trying to move detecting elements to the top of the system; and detecting the presence of a target molecule in the flowing gas or liquid wherein the presence of the target molecule disrupts the balance of the first and second forces causing the detecting element to exit the system wherein the release of the detecting element indicates the presence of the target molecule.

2. The method of claim 1, wherein the balance of the first and second forces is disrupted by the binding together of the target molecule with the detecting element and thereby changing the density or face area of the resulting complex.

3. The method of claim 1, wherein the balance of the first and second forces is disrupted by the cross-linking of detecting elements or the breaking apart of previously cross-linked detecting elements.

4. The method of claim 1, wherein the first force is magnetic, electrical, acceleration, or any combination thereof.

5. The method of claim 1, wherein the detecting elements are inert particles or living cells.

6. The method of claim 1, wherein the detecting elements are polymer beads, paramagnetic beads, glass beads, or a combination thereof, wherein the surface of the beads have antibodies, nucleic acids, complexes, or any combination thereof.

7. The method of claim 1, wherein it is unnecessary to separate debris from the flowing fluid.

8. The method of claim 1, wherein the release of the detecting element is detected by some means.

9. The method of claim 8, wherein the detecting element is detected by absorption, fluorescence, colorimetric assay, change in magnetic signature, or any combination thereof.

10. The method of claim 1, wherein the released detecting element may be captured, concentrated, or both for further evaluation.

* * * * *